United States Patent [19]

Shine

[11] Patent Number: 5,078,693
[45] Date of Patent: Jan. 7, 1992

[54] SAFETY HYPODERMIC SYRINGE

[76] Inventor: Jerry P. Shine, 10451 Isleworth Ave., San Diego, Calif. 92126

[21] Appl. No.: 496,253

[22] Filed: Mar. 20, 1990

[51] Int. Cl.$^5$ ............................................. A61M 5/32
[52] U.S. Cl. ................................... 604/192; 604/263
[58] Field of Search ...................... 604/192, 187, 263

[56] References Cited

U.S. PATENT DOCUMENTS

| 4,820,277 | 4/1989 | Norelli | 604/192 |
| 4,976,699 | 12/1990 | Gold | 604/192 |

FOREIGN PATENT DOCUMENTS

| 2618685 | 3/1989 | France | 604/192 |

*Primary Examiner*—John D. Yasko
*Attorney, Agent, or Firm*—Calif Tervo

[57] ABSTRACT

According to the invention a hypodermic syringe includes a needle guard that prevents accidental puncture by the needle. The guard includes a fixed leaf that is attached to the needle hub and a hinged leaf that is hingedly attached to the fixed leaf. The hinged leaf is moveable from a shielding position wherein shield the needle tip to a retracted position wherein the needle tip is exposed for insertion. A spring biases the hinged leaf in the shielding position. A trigger attached to the hinged leaf is activated by the user to move the hinged leaf the retracted position.

4 Claims, 1 Drawing Sheet

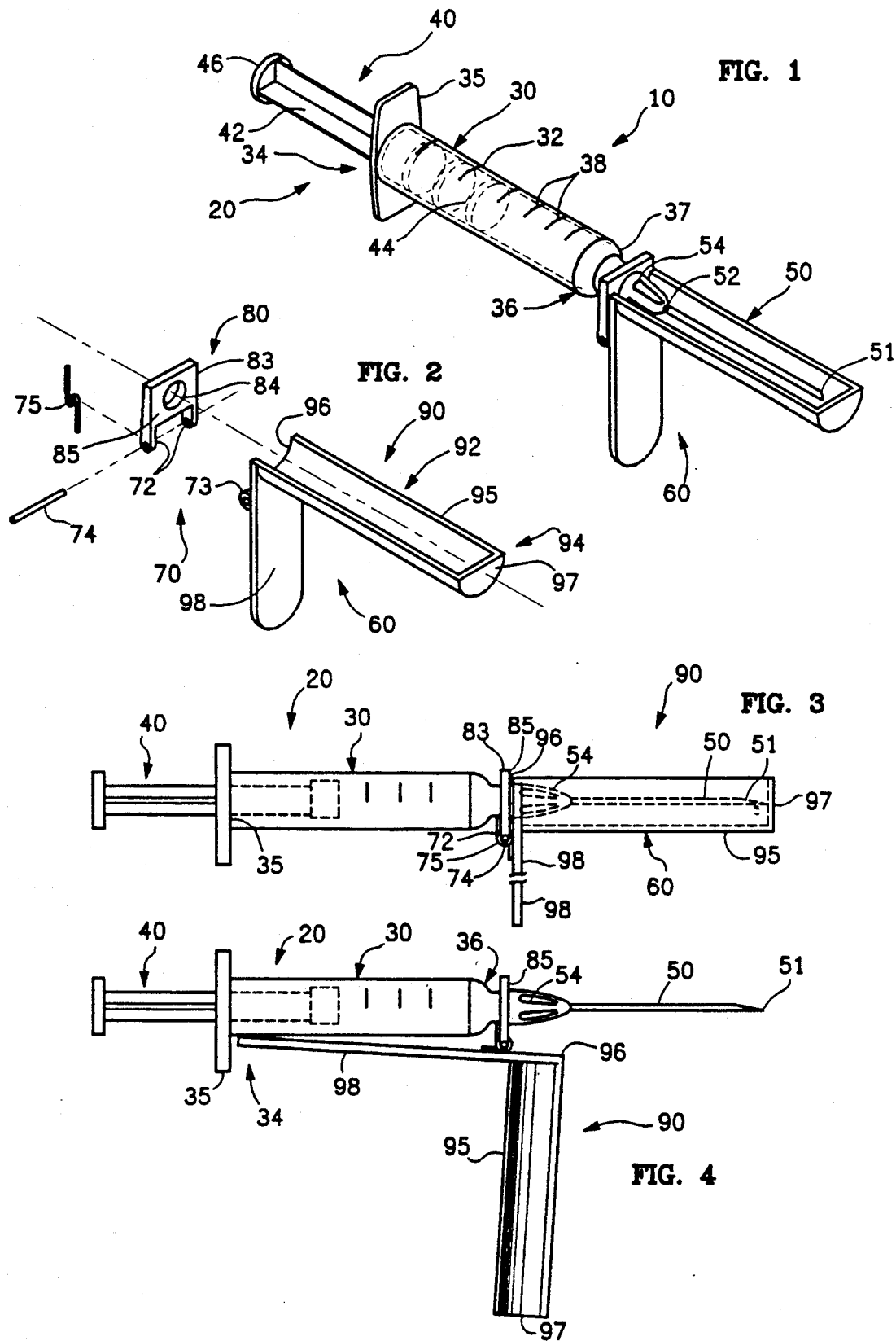

SAFETY HYPODERMIC SYRINGE

BACKGROUND OF THE INVENTION

1. Field of the Invention

This invention relates to a needle guard for a hypodermic syringe to prevent accidental puncture by the needle. More particularly, the needle guard is mounted on the syringe and includes a movable, needle shielding portion which is biased in the shielding position.

2. Background of the Invention

Accidental puncture of a person by a hypodermic syringe needle may result in passage the inadvertent transfer of disease organisms.

A hypodermic syringe needle often comes with a protective sleeve cover to prevent contamination and accidental puncture. However, once the sleeve is removed, it is often not replaced. Also, directly following the use of the syringe, to say draw blood, the needle tip is exposed and a person my be accidentally punctured should the syringe by dropped or mis-handled.

Therefore, it is desirable to have a device capable of shielding the needle tip from accidentally puncturing someone whenever the needle is not directly in use.

SUMMARY OF THE INVENTION

According to the invention a hypodermic syringe includes a needle guard that prevents accidental puncture by the needle. The guard includes a fixed leaf that is attached to the needle hub and a hinged leaf that is hingedly attached to the fixed leaf. The hinged leaf is moveable from a shielding position wherein shield the needle tip to a retracted position wherein the needle tip is exposed for insertion. A spring biases the hinged leaf in the shielding position. A trigger attached to the hinged leaf is activated by the user to move the hinged leaf the retracted position. In an exemplary embodiment, the trigger, in the retractor position, is sufficiently long to be held by a user's finger adjacent a finger flange on the upper end of the hypodermic syringe.

Other features and many attendant advantages of the invention will become more apparent upon a reading of the following detailed description together with the drawings in which like reference numerals refer to like parts throughout.

BRIEF DESCRIPTION OF THE DRAWING

FIG. 1 is a perspective view of the safety hypodermic syringe of the present invention including a needle guard.

FIG. 2 is a perspective exploded view of a preferred embodiment of the needle guard of FIG. 1.

FIG. 3 is a side view of the safety hypodermic syringe of FIG. 1 showing the needle guard in the shielding position.

FIG. 4 is a side view of the safety hypodermic syringe of FIG. 1 but showing the needle guard in the retracted position.

DETAILED DESCRIPTION OF THE INVENTION

With reference now to the drawings, and more particularly to FIG. 1 thereof, there is shown a safety hypodermic syringe, denoted generally as 10, of the present invention. The safety hypodermic syringe generally comprises a hypodermic syringe, denoted generally as 20, and a needle guard, denoted generally as 60.

Hypodermic syringe 20, shown, is intended to be of a common type such as is used for injecting drugs into a patient or for removing fluids from a patient. Although, a specific configuration of hypodermic syringe is shown and described, it is understood that the needle guard 60 may be used in conjunction with hypodermic syringes of different configuration. Hypodermic syringe 20 is comprised generally of barrel 30, plunger 40, and needle 50. Barrel 30 has a tubular portion 32 of transparent or translucent material creating a chamber such that the quantity of fluid therein can be visually ascertained. Scale markings 38 on tubular portion 32 indicate the amount of fluid therein. Barrel upper end 34 includes an opening to accommodate a plunger 40 and a finger flange 35 which aids in controlling the operation of plunger 40. Plunger 40 includes shaft 42, stopper 44, and thumb rest 46.

Barrel lower end, denoted generally as 36, commonly necks down and includes a locking tip 37 for accommodating the attachment of needle 50.

The inner end 52 of needle 50 is retained in needle hub 54 which is attached to locking tip 37 on the syringe lower end 36. Needle hub 54 is commonly made of metal or hard plastic. Needle hub 54 retains needle 50 in fluid communication with the barrel chamber. Needle hubs typically have a circular cross-section near the attachment of the locking tip of about the same diameter of the locking tip and commonly slightly taper outwardly, i.e. away from barrel 30, as shown best in FIG. 4.

Needle 50 shown is of the cannula type having an axial central bore therethru and a pointed outer end 51.

Needle guard 60 attaches to hypodermic syringe 10 and shields needle tip 51 so that a person cannot be accidently pricked by the needle tip 51. Needle guard 60 is comprised generally of attachment portion 80 for attaching the guard 60 to a syringe 20, movable leaf means 90 including hinged leaf 92 for shielding the needle tip 51, and a movable attachment means for connecting the attachment portion 80 to movable leaf means 90 such that the moveable leaf means 90 is moveable from a position shielding needle tip 51 to a retracted position exposing the needle tip for insertion. Needle guard 60 may be made of any suitable materials such as strong plastic.

FIG. 2 is a perspective exploded view of an exemplary embodiment of needle guard 60 of the present invention. Needle guard 60 includes an attachment portion, denoted generally as 80, for attaching the needle guard 60 to syringe 20. Attachment portion 80 includes fixed leaf means, such as fixed leaf 83, including attachment means, such as bore 84 through the fixed leaf 84, for attaching fixed leaf 83 to syringe 20. In the preferred embodiment, shown, bore 84 is configured to be slideably attached over needle hub 54 and to friction fit thereon such that it will remain in position during normal use and operation of the hypodermic syringe 20.

Movable attachment means, denoted generally as 70, includes hinge means, denoted generally as 71, for hingedly attaching hinged leaf 92 to attachment portion 80. Hinge 70 includes hinge knuckles 72 on fixed leaf 83, mating knuckles 73 on movable leaf means 90, and hinge pin or pintle 74 for passing thru the knuckle bores. Biasing means, such as spring 75, bears against fixed leaf 83 and movable leaf 90 to bias the moveable leaf in the shielding position. Other movable attachment means and biasing means are contemplated. For example, the biasing means could be a detent device, snap, or catch between the moveable leaf means and the attachment portion. Or, the hinge means could be the common plastic press fit hinge with adjacent knuckles having mating protrusions and cavities. Also, both functions may be performed by use of a single resilient biasing member, such as of spring steel or plastic, connecting the parts.

Moveable leaf means 90 generally includes hinged leaf 92 including a shielding portion 94 that, in the shielding position, is disposed near the needle tip 51 such that an object approaching the needle tip encounters shielding portion 94 and not the needle tip 51. Hinged leaf 92 includes a semi-circular channel 95 having an inner end face 96 that, in the shielding position, abuts the outer face 85 of fixed leaf 83 and terminates in closed end 97 covering needle tip 51. As best seen in FIG. 3, in the shielding position, needle 50 is disposed within channel 95.

Movable leaf retraction means, such as trigger 98, is attached to the inner end of hinged leaf 92 as a means for the user of the hypodermic syringe 20 to easily move moveable leaf means 90 to the retracted position and retain it there during insertion of the needle. Trigger 98, shown, is disposed to channel 95 at approximately a right angle. Trigger 98 and the inner end of hinged leaf 92 are connected at knuckles 72 so that movement of trigger 98 in an arc moves the hinged leaf 92 in a corresponding arc.

FIG. 3 is a side view illustrating the safety hypodermic syringe 10 with the needle guard in the needle shielding position. One end of spring 75 bears against trigger 98 and biases moveable leaf 90 in the position shown. Preferably, a stop means, such as channel inner end face 96 bearing against fixed leaf outer face 85, prevents the moveable leaf 90 from bearing on the needle 50 or needle tip 51.

FIG. 4 is a side view identical to FIG. 3 except for the movable leaf 90 being rotated about hinge 71 to the retracted position such that needle 50 is exposed for insertion. The outer end of trigger 98 may bear against barrel 30 to prevent further rotation about hinge 71. In use, trigger 98 would be activated by the first finger of the user. Typically, the user grips the syringe barrel 30 with one hand and moves the trigger rearward with the fore finger to the retracted position to expose the needle tip 51 for insertion, such as into a patients vein. Preferably, in the retracted position, trigger 98 contacts barrel 30 so that a user, by firmly gripping trigger 98 simultaneously grips barrel 30. In this manner, no extra user's fingers are needed to hold trigger 98 in the retracted position. Preferably, also, trigger 98 is of sufficient length so as to extend at least to the proximity of finger flange 35 on barrel upper end 34 as seen in FIG. 4. Commonly, syringe 20 is held with first and second fingers on opposite sides of barrel 30 and abutting finger flange 35. Thus, trigger 98 of the length shown in FIG. 4 may be held in the retracted position shown by one of the fingers adjacent finger flange 35. If trigger 98 is held by a single finger adjacent finger flange 35, a slight rotation of syringe 20, typically accomplished by simply extending one holding finger and retracting the other, will release trigger 98. Whenever the needle is not inserted, hinged leaf 92 moves to the shielding position immediately upon release of trigger 98.

Thus, it is seen that the invention provides a novel method of preventing accidental puncture by a hypodermic syringe needle. Whenever the hypodermic syringe is dropped or left unattended, the needle is shielded.

Although a particular embodiment of the invention has been illustrated and described, various changes may be made in the form, construction, and arrangement of the parts without sacrificing any of its advantages. Therefore, it is to be understood that all matter herein is to be interpreted as illustrative and not in any limiting sense, and it is intended to cover in the appended claims such modifications and changes as come within the true spirit and scope of the invention.

I claim:

1. A safety hypodermic syringe including:
   a hypodermic syringe including:
      a barrel having:
         an upper end including:
            a finger flange; and
         a needle end; and
      a needle having:
         an inner end attached to said barrel needle end; and
         a tip end; and
      a needle guard attached to said syringe comprising:
         attachment means for movably connecting a movable leaf means to said syringe;
         movable leaf means including:
            an inner end; and
            a shielding portion;
   said movable leaf means movably attached by said attachment means to said syringe such that said movable leaf means is movable between a shielding position whereby said shielding portion shields said needle tip end and a retracted position whereby said shielding portion is disposed away from said needle tip end; and
      trigger means attached to said movable leaf means near said inner end thereof for moving said movable leaf means to the retracted position in response to a force applied to said trigger means by a user of said hypodermic syringe; said trigger means being so attached and being of sufficient length such that said trigger means in the retracted position extends to the proximity of said finger flange such that a single finger of a user may simultaneously bear against said finger flange and retain said trigger means in the retracted position.

2. The safety hypodermic syringe of claim 1 wherein said needle guard further includes:
   biasing means for biasing said movable leaf means in the shielding position such that upon release of said trigger means by a user's finger said movable leaf means will return to the shielding position.

3. The safety hypodermic syringe of claim 1 wherein:
said attachment means includes:
   bore means for receiving said syringe for attaching said attachment means to said syringe.

4. The safety hypodermic syringe of claim 3 wherein:
   said hypodermic syringe includes needle hub means for mounting said needle to said barrel; and
   said bore means is adapted for receiving and for attachment to said needle hub.

* * * * *